United States Patent [19]

Peterson et al.

[11] Patent Number: 5,425,381
[45] Date of Patent: Jun. 20, 1995

[54] PEDIATRIC RESTRAINT AND CUSHION

[76] Inventors: Vacharee S. Peterson; Catherine T. Boler, both of 1224 Arcade St., St. Paul, Minn. 55106

[21] Appl. No.: 349,243
[22] Filed: Dec. 5, 1994
[51] Int. Cl.[6] ............................................. A61B 19/00
[52] U.S. Cl. ................................... 128/869; 128/876
[58] Field of Search ............... 128/845, 846, 869–876; 5/630, 632, 633, 636, 647, 648, 628, 655, 424

[56] References Cited

U.S. PATENT DOCUMENTS

| | | | |
|---|---|---|---|
| 2,175,748 | 10/1939 | Dunn | 5/628 |
| 2,639,206 | 5/1953 | Butler | 128/869 |
| 2,856,614 | 10/1958 | O'Leary | 5/633 |
| 2,995,407 | 8/1961 | Izzi | 128/873 |
| 3,565,419 | 2/1971 | Allard | 5/633 |
| 3,641,997 | 2/1972 | Posey | 128/873 |
| 3,814,414 | 6/1974 | Chapa | 128/873 |
| 4,383,713 | 5/1983 | Roston | 5/655 |
| 5,129,406 | 7/1992 | Magnusen | 128/873 |

Primary Examiner—Michael A. Brown
Attorney, Agent, or Firm—Thomas B. Tate

[57] ABSTRACT

A combination pediatric restraint and cushion for a dental patient. The restraint is made of cloth with an adhesive backing, and has a plurality of flaps with hook and loop fasteners, a plurality of straps, and a headpiece. The cushion is encased in a pillowcase which has an adhesive backing and has flaps with hook and loop fasteners, and has an arcuate indentation at its top end.

1 Claim, 4 Drawing Sheets

PEDIATRIC RESTRAINT AND CUSHION

SUMMARY AND BACKGROUND OF THE INVENTION

When a pediatric dental patient is restless and uncooperative, it is often necessary for the dentist to use a restraining device to hold the child in position in the dental chair long enough for the dentist to complete the necessary work. The two devices most commonly used for this purpose are the Olympic Papoose Board manufactured by Olympic Medical, which is a Velcro wrap which has armholes and a stiff board upon which the child's back rests, and the Pedo-Wrap manufactured by Clark Associates, which is a stiff pillow device with a mesh and Velcro screen wrap. Although these devices are fairly effective in preventing lateral movement, it is possible for the child to slide downward in the dental chair if he kicks in an attempt to escape, and in addition these devices are uncomfortable for the child due to their stiffness.

An object of the present invention is to provide an effective restraint system which is also comfortable and relaxing for the child patient. The invention is made of soft cloth, and has a first piece which has Velcro flaps which around the torso to comfortably restrain the patient, a headpiece which fits over the dental chair and straps which fit around the dental chair, and a second piece in which a cushion fits around the patient's buttocks and has flaps which fit around the patient's legs. Both the first piece and the second piece have an adhesive backing to prevent the patient from sliding in the dental chair.

Another object of the invention is to allow an adult size dental chair to be converted for use for any size patient, including children.

DESCRIPTION OF THE PREFERRED EMBODIMENT OF THE INVENTION

Figure 1:
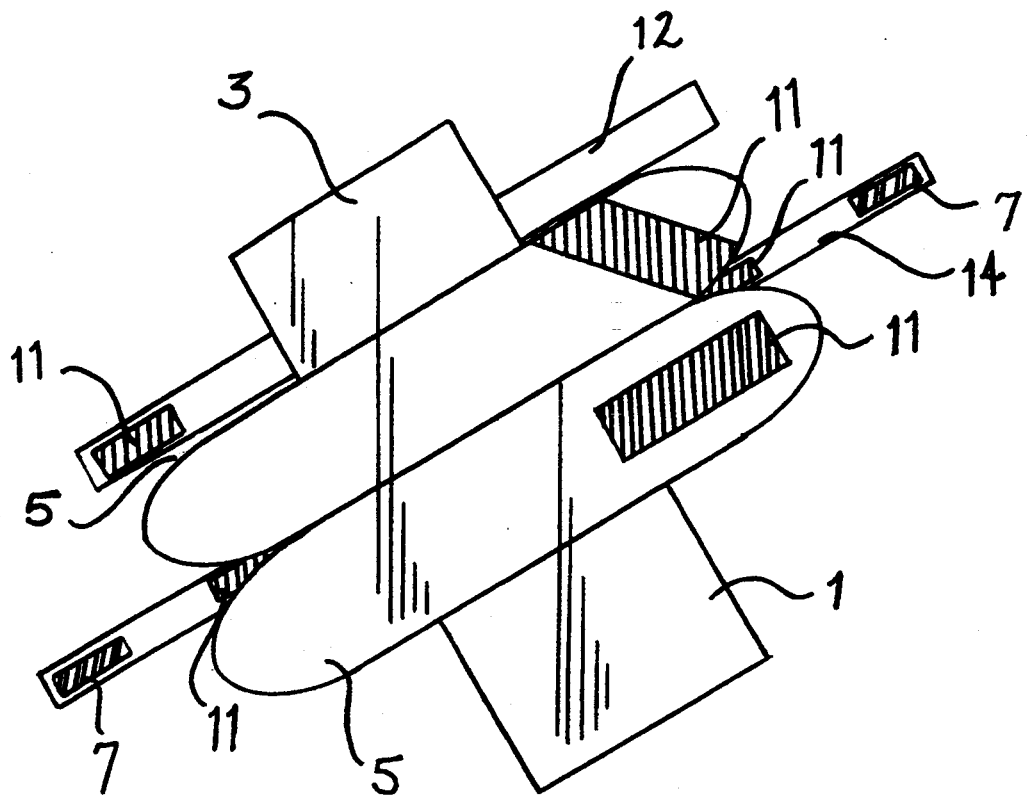
FIG. 1 is a top perspective view of the front side of the restraint.
Figure 2:
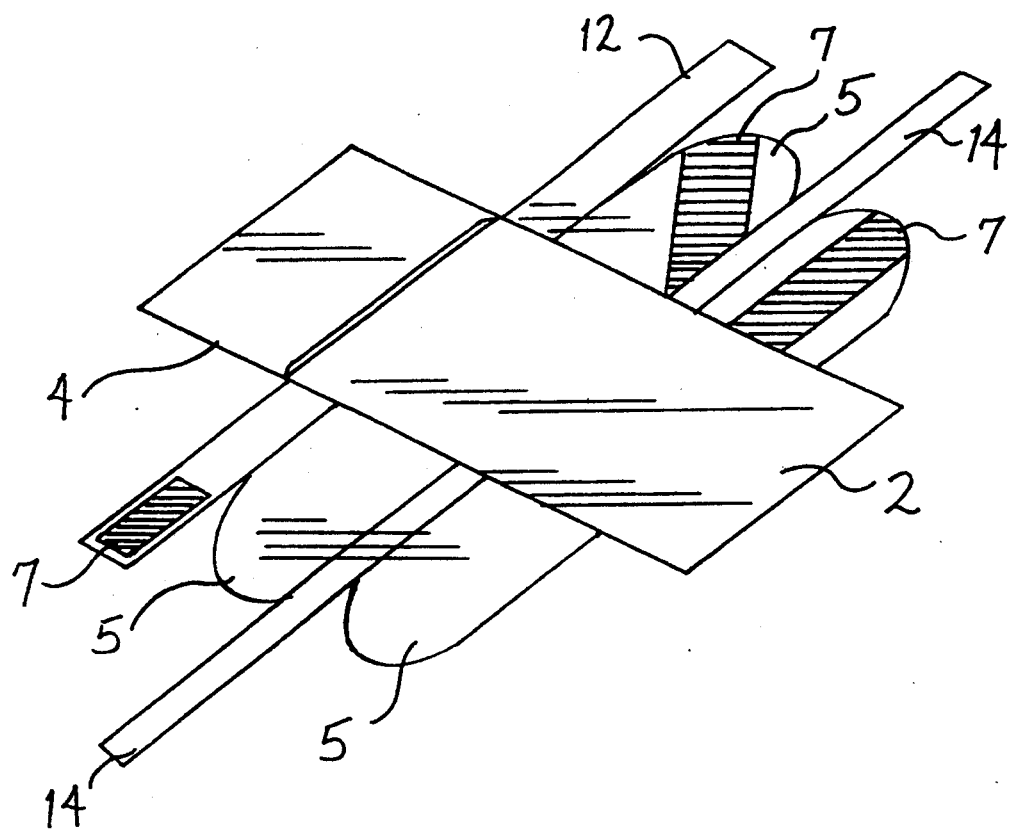
FIG. 2 is a top perspective view of the back side of the restraint.
Figure 3:
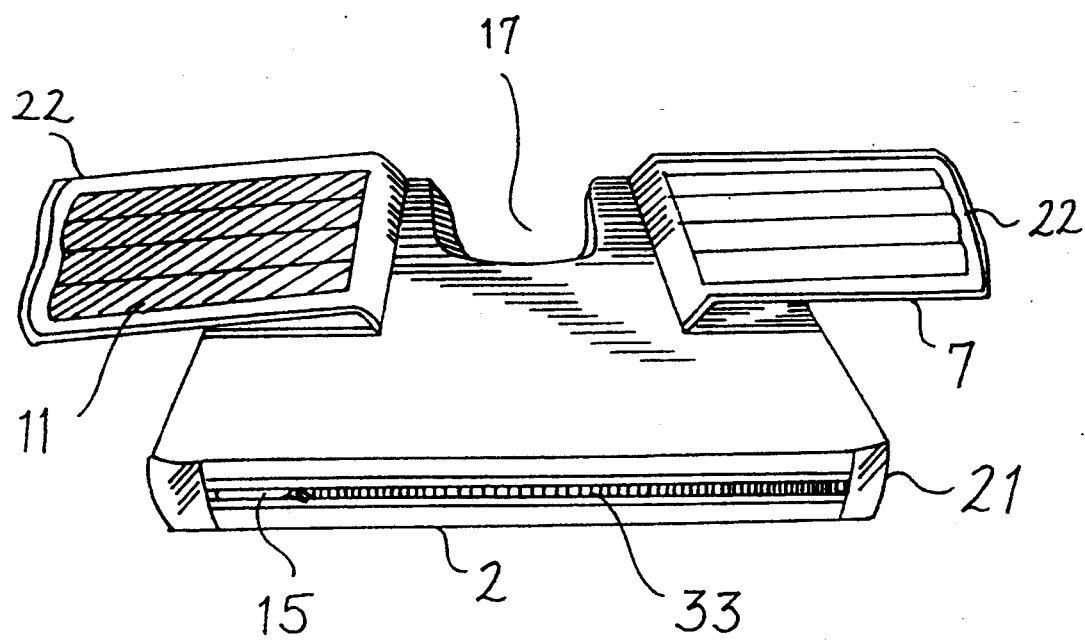
FIG. 3 is a top and front perspective view of the cushion.
Figure 4:
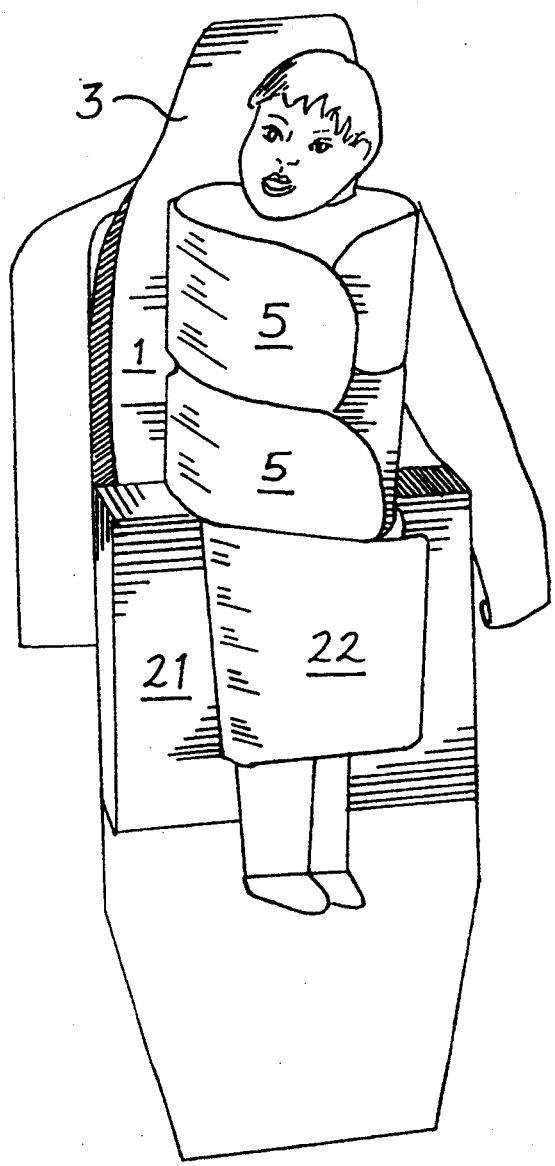
FIG. 4. is a top view of the device in use on a patient in the dental chair.

The invention is a combination restraint and cushion for use in holding a child patient comfortably in position on a dental chair. It is made of soft cloth material, with the various pieces cut from patterns and then assembled by sewing.

The restraint comprises a generally rectangular main body portion 1 which has a non-slip rubber backing 2 which adheres to the vinyl of the dental chair to create traction. Attached to the top of the main body portion 1 is a headpiece 3 which has a Lycra flap 4 which fits over the top of the dental chair. Two pair of horizontal flaps 5 are attached to the center of the main body portion 1 parallel to each other and extend beyond the outer edges of the main body portion 1. Each flap 5 is provided with hook and loop fastener (Velcro) pads arranged with the loop fastener 7 affixed to the bottom of one flap and the hook fastener 11 affixed to the top of the opposite flap 5, so that when the flaps 5 are folded inward over the patient's torso, the hook fastener 11 contacts the loop fastener 7, with the hook fastener 11 on top. A plurality of straps 12 are used to secure the restraint to the dental chair. One pair of straps 12 is attached to the headpiece 3 and ties around the head of the dental chair by connecting the hook fastener 11 affixed to the top of one strap 12 with the loop fastener 7 affixed to the bottom of the other strap 12. Another pair of straps 14 (or alternatively two pair) is attached to the main body portion 1 and ties around the armrests of the dental chair (or the back of the chair if there are no armrests) by means of hook and loop fasteners arranged such that each strap 14 has a hook fastener 11 at its proximal end and a loop fastener 7 at its distal end.

The cushion 15 is preferably about four inches thick, is generally rectangular with an arcuate indentation 17 at the top end which holds the child's buttocks and counteracts the effect of gravity by preventing the child from sliding downward in the dental chair. The cushion 15 is encased in a similarly shaped pillowcase 21 which has a zipper 33 to allow the cushion 15 to be removed for washing and which has a non-slip rubber backing 2 to adhere to the vinyl of the dental chair. A pair of flaps 22, having a hook fastener 11 on one and a loop fastener 7 on the other, is attached to the pillowcase 21 and folds together to hold the child's legs in position. If the dental chair lacks armrests, straps can be attached to the pillowcase 21 to be tied around the chair. The cushion 15 can be adjusted to accommodate different size children by overlapping it on the main body position 1 of the restraint to the length desired.

As an optional feature, a pair of Velcro strips may be provided on each of the pieces (loop Velcro on the top surface of the lower part of the main body portion 1 of the restraint and hook Velcro on the rubber backing 2 of the pillowcase 21 covering the cushion 15) so as to enable the cushion to not only be overlapped onto the restraint, but also to be attached to the restraint, thereby preventing sliding to an even greater extent.

Another optional feature is that slide locks or buckle closures may be used instead of Velcro to fasten straps 12 to the chair or to fasten straps 14 to the chair.

We claim:

1. A combination restraint and cushion for securing a pediatric patient in a dental chair, said combination comprising:

a restraint comprising a main body portion which has a plurality of flaps attached thereto, each of said flaps having hook and loop fasteners affixed thereto, such that said flaps can be positioned and fastened around said patient to hold said patient's torso in position, a plurality of straps for tying said restraint around said dental chair, and a headpiece which fits around the top of said dental chair, said restraint having adhesive material affixed to the back thereof to hold said restraint in position on said dental chair;

and a cushion having an arcuate indentation at its top end to hold said patient's buttocks in position, said cushion being enclosed in a pillowcase having an adhesive material affixed to the underside thereof in order to maintain said cushion in position on said dental chair, said pillowcase having a plurality of flaps attached thereto, said flaps each having hook and loop fasteners affixed thereto such that said flaps can be positioned and fastened around said patient's legs to hold them in position.

* * * * *